United States Patent [19]

Rubin

[11] Patent Number: 5,034,415
[45] Date of Patent: Jul. 23, 1991

[54] TREATMENT OF DIABETES MELLITUS

[75] Inventor: David Rubin, San Diego, Calif.

[73] Assignee: Century Laboratories, Inc., Port Washington, N.Y.

[21] Appl. No.: 428,421

[22] Filed: Oct. 30, 1989

Related U.S. Application Data

[63] Continuation of Ser. No. 82,498, Aug. 7, 1987, abandoned.

[51] Int. Cl.$^5$ ............................................. A61K 31/20
[52] U.S. Cl. ................................... 514/560; 514/866
[58] Field of Search .............................. 514/560, 866

[56] References Cited

U.S. PATENT DOCUMENTS

| | | | |
|---|---|---|---|
| 4,472,432 | 9/1984 | Iwamura et al. | 424/318 |
| 4,511,575 | 4/1985 | Holland | 514/532 |

FOREIGN PATENT DOCUMENTS

| | | | |
|---|---|---|---|
| 115419 | 1/1984 | European Pat. Off. | |
| 0132089 | 1/1985 | European Pat. Off. | 514/560 |
| 175468 | 3/1986 | European Pat. Off. | 514/560 |
| 181689 | 5/1986 | European Pat. Off. | 514/560 |
| 2418218 | 11/1975 | Fed. Rep. of Germany. | |
| 2459515 | 6/1976 | Fed. Rep. of Germany. | |
| 3232036 | 3/1983 | Fed. Rep. of Germany. | |
| 248610 | 12/1985 | Japan | 514/560 |
| 2033745 | 5/1980 | United Kingdom. | |
| 1604554 | 12/1981 | United Kingdom. | |

OTHER PUBLICATIONS

Thromb, Haemostas 48(3), 344 (1982).
Thrombosis Res. 43; 643–655, 1986.
Boustani et al., "Enteral Absorption in Man of Eicosapentaenoic Acid in Different Chemical Forms", *Lipids*, vol. 22, No. 10, 1987.
Lawson et al., "Human Abscription of Fish Oil Fatty Acids as Triacylclycerides, Free Acids, or Ethyl Esters", *Biochem. Biophys. Res. Commun.*, 152(1), 328–335, 1988.

*Primary Examiner*—Frederick E. Waddell
*Assistant Examiner*—Diane Gardner
*Attorney, Agent, or Firm*—Browdy and Neimark

[57] ABSTRACT

Free fatty acids from fish oils, DHA and EPA, are useful in treating diabetes mellitus. The free fatty acids were an order of magnitude more effective in treating diabetes than unhydrolyzed fatty acids derived from fish oil.

10 Claims, No Drawings

TREATMENT OF DIABETES MELLITUS

FIELD OF THE INVENTION

The present invention relates to a composition for treatment of diabetes mellitus.

BACKGROUND OF THE INVENTION

Diabetes mellitus is a disease of the pancreas which exhibits an increased level of blood sugar as the essential symptom. In most cases, it is not only the beta-islet cells that are affected, but the entire pancreas, so that one might expect there to be a deficiency of all of the pancreatic enzymes, including lipases. It is manifested by an insufficient amount of the pancreatic hormone insulin being released.

At present, the natural hormone is, as a rule, replaced by animal insulin isolated from the glands of slaughtered animals, or human insulin, which is accessible semisynthetically from porcine insulin or by genetic engineering methods.

Two fundamentally different ways have hitherto been taken in the use of genetic engineering methods: separate synthesis of A and B chains and their subsequent chemical recombination, and synthesis of pre-proinsulin, the naturally occurring precursor of insulin. In the proinsulin molecule, the A and B chains are linked by a connecting piece, the C peptide. According to current theory, the most important function of this piece is spatial fixing of the two chains relative to one another, so that correct folding can take place. When folding has taken place, the three disulfide bridges are linked, and the unmodified three-dimensional structure of the insulin is thus stabilized. The C peptide is split off by enzymes having a tryptic and carboxypeptidase B activity. The splitting sites are predetermined by a Lys-Arg sequence (before the N-terminus of the A chain) or and Arg-Arg sequence (at the C-terminus of the B chain). Only free insulin has full biological activity, because part of the molecule is probably masked in the presence of the C peptide.

The particular chemical nature of insulin means that therapy is as a rule parenteral; the hormone would be completely degraded even before it was able to act, for example, on passage through the stomach and intestine. However, degradation reactions, essentially by various, relatively non-specific proteolytic enzymes, also take place at the injection site and in the circulation. The short in vivo half life of only about 7 minutes which thereby results is in principle appropriate from the physiological point of view in the context of homeostasis; however, therapy is thereby made considerably more difficult, because the diabetic must typically inject himself four times daily, as a rule shortly before mealtimes.

Early attempts have accordingly already been made to impart a protracted action to the insulin. The most successful so far have been those methods in which the insulin is converted into a paringly soluble state by addition of a depot auxiliary. Depot auxiliaries include, above all, divalent zinc ions, in the presence of which the insulin can be in crystalline or amorphous form in a neutral medium. The addition of basic proteins, for example, protamine sulfate or human globin, has the same effect, since insulin is an acid molecule with an isoelectric point $p_I$ of 5.4: basic protein and insulin are in the form of a crystalline or amorphous salt-like, sparingly soluble complex in the neutral range.

It is imagined that the slow release of the insulin from these sustained release formulations takes place by dilution, i.e., diffusion, of individual components which build up the crystal or the amorphous precipitate, or, in the case of insulin complexes with basic proteins, by proteolytic degradation of the depot excipient.

Human proinsulin, either by itself or in combination with the customary depot additions, has recently also been discussed as a delayed action principle, cf. German Patent No. A 3,232,036. The theory is that the proteolytic splitting of the C peptide is delayed in vivo and hence the fully active hormone is released from the proinsulin, which has only little inherent biological activity (about ⅛ of the activity of insulin, based on the amount of protein). Only those proinsulins which are identical or very similar in their sequence to that from humans are acceptable for use in humans. As is generally known, porcine and bovine proinsulin are immunogenic. The exact mode of action of proinsulin, however, is at present still open. It has in no way been proven that insulin is specifically released. On the contrary, degradation in vivo will take place in several ways, with production of in most cases inactive fragments. The therapeutic use of pro-insulin could thus rather be found, if at all, at the receptor level.

Diabetes therapy is characterized by individual influence factors, such as differences in the characteristics of the subcutaneous tissue, and also specific eating habits, physical activities, and many others besides. It is thus absolutely essential for good adjustment of the blood sugar to have available a number of insulin products with different action characteristics which are adapted to the individual requirements. In connection with non-optimum adjustment, in particular the topic of delayed diabetic damage is an issue. The immediate objective and subjective effects include hyper- or hypoglycemia, and macro-and micro-angiopathy, neuropathy, bephropathy, and retinopathy.

Besides pure delayed action insulin, so-called intermediate acting insulins have above all proven to be preparations which are optimally suited to the requirements of the patient. These are mixtures of a delayed action component and a component having an immediate and short action. Such mixtures are in general complicated multiphase systems which remain stable over a long period only when mixed in relatively narrowly defined proportions. Thus, for example, a suspension of 2-zinc-insulin crystals from pigs is not freely miscible with dissolved porcine insulin. The admixed, dissolved insulin precipitates immediately or in the course of time because of the relatively high zinc content which is necessary to stabilize the crystals. Such mixtures are stable within narrow limits if bovine insulin or a mixture of dissolved porcine insulin and phenylalanine (B1)-porcine insulin is used as the dissolved insulin, as disclosed in German patents No. A 2,418,218 and A,2,459,515. From the point of view of miscibility with dissolved insulin, protamine-insulin formulations are more advantageous, if crystals of protamine and insulin are used in an isophane ratio as the delayed action components.

Despite the early discovery of insulin and the later discovery and use of sulfonylureas (e.g., chlorpropamide, tolbutamide, acetohexamide, tolazamide, and biguanides such as phenformin) as oral hypoglycemic agents, the treatment of diabetes is less than satisfactory.

Because the use of insulin for treating diabetes requires multiple daily dosages, it is necessary to estimate frequently the amount of sugar in the urine or in the blood. The administration of an excessive dose of insulin causes hypoglycemia, with effects ranging from mild abnormalities in blood glucose to coma, or even death. Where effective, synthetic hypoglycemic agents are preferred over insulin, since they are more convenient to administer and are less prone to cause severe hypoglycemic reactions. However, the clinically available hypolglycemics are fraught with other toxic manifestations which limit their use. In any event, where one of these agents may fail in an individual case, another may succeed. The need for additional hypoglycemic agents, which may be less toxic or succeed where others fail, is clearly evident.

One attempt to provide non-insulin treatments for diabetes is disclosed by Holland, in U.S. Pat. No. 4,511,575. Holland discloses that certain pyrrolecarboxylic and pyrroleacetic acid derivatives substituted on the pyrrole ring with thioether groups, acyl groups, phenyl, substituted phenyl, phenoxy, substituted phenoxy, benzyl, or halo and optionally substituted on the pyrrole nitrogen with alkyl, and the pharmaceutically acceptable salts thereof can be used to lower the blood glucose levels of hyperglycemic animals.

Iwamura et al., in U.S. Pat. No. 4,472,432, disclose the use of alpha, beta-unsaturated higher fatty acids of the formula

$$CH_3(CH_2)_nCH=CHCOOH$$

wherein n represents 10, 12, 14, or 16, and pharmaceutically acceptable salts thereof. These fatty acids, which are extracted from freshwater clams, are said to be effective treatments for diabetes.

Since diabetics are thought to have more agreeable platelets with a shorter life span than nondiabetics, studies have been conducted on reducing platelet activity of diabetics with fish oil.

Vclardo et al., in *Thromb. Haemostas* 48 (3) 344 (1982) disclose that platelet activity in diabetics can be decreased by administration of high quantities of fish oil or eicosapentaenoic acid.

Haines et al., in *Thromb. Res.* 43: 643-655, 1986, disclose that a fish oil supplement was effective in reducing thromboxane production by platelets stimulated by collagen in diabetics. The fish oil supplements also increased plasma LDL cholesterol, fibrinogen, and clotting factor X in the group who took the fish oil supplement.

Neither of the two references above discloses any change in the blood glucose levels of the diabetics receiving fish oil.

The active ingredients in fish oil are (all-Z)-5,8,11,14,17-eicosapentaenoic acid (hereinafter EPA) and 22:6 omega3-docosahexaenoic acid (hereinafter DHA). EPA and DHA are known to be precursors in the biosynthesis of the prostaglandin PGE₃.

It is disclosed in British Patents Nos. 1,604,554 and 2,033,745 that EPA can be used to treat effectively, or to provide effective prophylaxis against, thromboembolic conditions such as myocardial infarctions, strokes, or deep vein thrombosis during surgical operations. These patents disclose the extraction of EPA from fish oil such as cod liver oil or menhaden oil. The EPA may be administered by replacing butter or ordinary margarine by a special margarine formulated so that in normal usage the recipient would receive the required amount of the EPA.

This process has not achieved widespread attention, despite the fact that it uses a natural substance which can readily be incorporated into the daily diet. One reason may be due to the difficulty of efficiently separating EPA from natural fish oils to obtain a pure product at reasonable cost. Another reason may be that the effects of administration of EPA are not as dramatic as anticipated.

Prostaglandins are a family of substances showing a wide diversity of biological effects. Prostaglandins of the 1-, 2-, and 3-series, respectively, incorporate one, two, or three double bonds in their basic 20-carbon carboxylic fatty acid structure which incorporates a 5-member cyclopentene ring.

The 1-series of prostaglandins are strong vasodilators, and inhibit cholesterol and collagen biosynthesis, as well as platelet aggregation. On the other hand, the 2-series prostaglandins are known to enhance platelet aggregation, cholesterol, and collagen biosynthesis, and also to enhance endothelial cell proliferation. The main effect of the 3-series prostaglandins, particularly PGE₃, is the suppression of the 2-series prostaglandins.

The precursor of the 2-series prostaglandins is arachidonic acid ((All-Z-5,8,11,14-eicosatetraenoic acid). DHLA is the precursor for the 1-series prostaglandins, and, as indicated hereinabove, EPA and DHA are precursors for the 3-series prostaglandins.

It is believed that EPA and DHA are effective precursors for prostaglandin PGE₃, which suppresses the 2-series prostaglandins. Additionally, EPA and/or DHA itself competes with arachidonic acid on the same enzymatic system and thus inhibits the biosynthesis of 2-series prostaglandins. This inhibition of the 2-series prostaglandins results in an increase of the ratio of PGE₁:PGE₂.

SUMMARY OF THE INVENTION

It is an object of the present invention to provide a treatment for diabetes.

It is a further object of the present invention to provide a treatment for diabetes that does not involve the injection and monitoring of insulin.

It is another object of the present invention to provide a treatment for diabetes that can be administered orally.

This an other objects of the present invention are accomplished by administering to patients suffering from diabetes an effective amount of free fatty acids obtained from fish oil and fish oil hydrolyzate.

It has been postulated that any medication which would interfere with the production of PGE₂ would influence the progress of diabetes. What is surprising, however, is the enormous difference between the fish oil in the form of the triglyceride, as it occurs naturally, and its free fatty acid form.

The effects of EPA and DHA on diabetes most probably has to do with metabolism of leukotrienes rather than, or in addition to, prostaglandin metabolism.

Arachidonic acid is metabolized by major enzymatic systems in the body to yield the leukotrienes.

In one system, cyclooxygenase metabolizes arachidonic acid to yield the prostaglandins. In another system, arachidonic acid is metabolized via the lipo-oxygenase pathway to yield the leukotrienes.

Similarly to the way that EPA and DHA compete with arachidonic acid on the cyclo-oxygenase route to produce PGE₃ rather than PGE₂, there is a completion on the 5-lipo-oxygenase to produce leukotrienes of the 5-family rather than the 4-family. It is believed that the leukotrienes $B_4$ and $D_4$ are associated with pathology of the pancreas, which the 5-leukotrienes counteract.

This difference may be accounted for by the fact that the triglyceride, even if completely hydrolyzed by pancreatic lipase, becomes re-esterified shortly after crossing the intestinal walls to become the triglyceride again. As the triglyceride, the compounds migrate to the adipose tissues surrounding the body. Thus, very little fatty acid is bioavailable. Free fatty acids, on the other hand, are readily absorbed, and are conjugated to serum albumin and thus are available to compete with arachidonic acid in different sites of the organism.

DETAILED DESCRIPTION OF THE INVENTION

Diabetes mellitus can be treated according to the present invention by administering to a patient suffering from diabetes the free fatty acid EPA or DHA or mixtures thereof obtained from hydrolyzed fish oils. Although when extracted from fish oils these acids are generally present in amounts of approximately 35% EPA/65% DHA, the acids can be administered in any combination thereof. The dose of the free fatty acids needed for therapeutic or prophylactic effect will vary with the route of administration and the nature and severity of the condition being treated, but it will generally be at least 0.5 gram, and preferably from 1.5 to 5 grams, per day. This is the dosage for an average kg adult male, and the dose for other patients will vary pro rata according to the weight of the patient, i.e., about 20-40 mg/kg.

The EPA and/or DHA need not be administered as the free fatty acids per se, but may be used in the form of their pharmaceutically acceptable salts. The preferred salts are the sodium or potassium salts, or any other pharmaceutically acceptable solid salt, as these are suitable for making into orally ingestible tablets.

While it is preferred to administer the free fatty acids of the present invention orally, as this is a convenient route for routine administration, the free fatty acids may be administered by any route by which it may be successfully absorbed, e.g., parenterally (i.e., subcutaneously, intramuscularly, or intravenously), rectally, vaginally, or topically, for example, as a skin ointment or lotion.

While it is possible for the free fatty acids to be administered as such, it is preferable to present them as a pharmaceutical formulation. The formulations, both for veterinary and for human medical use, of the present invention comprise the free fatty acids as defined, together with one or more pharmaceutically acceptable carriers therefor and, optionally, other therapeutic ingredients, although other unsaturated fatty acids should be avoided. The carriers must be pharmaceutically acceptable in the sense of being compatible with the other ingredients of the formulations and not deleterious to the recipient thereof. Formulations include those suitable for oral, rectal, vaginal, intrapulmonary, or parenteral (including subcutaneous, intramuscular, and intravenous) administration. Formulations for oral administration, such as tablets or capsules, are preferred.

The free fatty acids of the present inventions may also be administered by replacing butter and/or ordinary margarine by a special margarine, e.g., of the emulsion type, formulated so that in normal usage the recipient would receive the required amount of the combination. Cooking oils and fats may also be similarly formulated to contain the composition of the present invention.

The EPA and DHA are separated from fish oil such as cod liver oil as described in copending application Ser. No. 810,550, entitled "A Method of Extraction and Purification of EPA and DHA from Natural Sources", the entire contents of which are hereby incorporated by reference.

The free fatty acids are obtained by first hydrolyzing the triglycerides of the oil source under mild conditions, such as by the use of the enzyme lipase, removing non-saponifiable material by washing with organic solvent, treating with urea in order to remove saturated and mono-unsaturated fatty acids to form a urea complex with saturated and mono-saturated fatty acids, dissolving the remainder in an organic solvent, preferably acetone, slowly cooling and fractionally removing solidified material as it forms. In a preferred embodiment, the use of extremely low temperatures to complete the precipitation of the pure fatty acids can be avoided by increasing the concentration of fatty acid in the solution after the formation and removal of each precipitate by evaporating a proportion of the solvent and then repeating the cooling step. In this manner, substantially the same yield and purity can be obtained without the use of extremely low temperatures which would make a commercial process less desirable.

The oil from which the EPA and DHA is separated by means of the present invention is preferably as fresh as possible so that the separation may occur before any substantial degradation of the fatty acids occurs. Natural fats or oils containing high levels of EPA and DHA suitable for use in the present invention include, for example, fats and oils of marine animals such as colored fish, such as the mackerel, sardine, mackerel pike and herring; cod liver oil; and marine animals such as krill and the various shrimp-like animals. It should be understood, however, that any source of EPA and DHA may be used in the present invention. Preferably the source fish are obtained from as cold an environment as possible. The optimal enzymatic activity for the enzyme 5-desaturase, which catalyzes the conversion of eicosatetraenoic acid to EPA, occurs at 90° C. Thus, fish from cold environments are higher in EPA than warmer water fish.

Furthermore, even greater yields of EPA can be obtained if the fish are raised in a controlled environment. If the fish are fed a diet rich in linolenic acid and maintained in salt water at 9° C., optimum amounts of EPA will be produced.

The natural fat or oil is subjected to saponification or alcoholysis in order to convert the triglycerides to free fatty acids or esters of fatty acids. The method selected, however, should be one in which high temperatures and strongly basic reagents are avoided, as these can lead to peroxidation and cis-trans conversion. The preferred method of hydrolysis is enzymatic hydrolysis using the enzyme lipase using a temperature of 35°-40° C. and pH of 6-7. The lipase should be activated by traces of cysteine or ascorbic acid, as is convention. Another advantage of the use of lipase for saponification is the fact that lipase enzyme, being stereo-specific, will not cleave any trans-fatty acids, which may be produced in nature from the triglycerides. Thus, even if there is trans-EPA or DHA in the starting material, it will be removed with the non-saponified material and will not be present in the final product.

An alternative method of hydrolyzing the natural fats and oils is by partially hydrolyzing these fats and oils with lipase or a strong base. When lipase is used, hydrolysis for 1½ to 2 hours, rather than for the usual six hours, provides a richer source of EPA because the lipase preferentially removes the first and third branches of the treated triglyceride. It is known that in natural triglycerides the outside branches have more greatly saturated chains than the middle branch. Thus, limiting the amount of hydrolysis automatically removes a substantial amount of the more saturated acids.

Potassium hydroxide can also be used to partially hydrolyze the natural fats or oils. The source of oil is treated with potassium hydroxide for about 15-20 minutes to partially hydrolyze the triglycerides. As in the case with lipase, this partial hydrolysis yields a richer source of EPA from the triglyceride because the first and third branches of the triglyceride are preferentially attacked by the base.

After the partial hydrolysis, sulfuric acid or other strong mineral acid such as hydrochloric acid or nitric acid is added to the hydrolysis mixture to separate out the mixture of fatty acids. The mixture of fatty acids floats to the top, and the bottom, aqueous, phase is discarded.

This partial hydrolysis step is also useful in improving the separation of other polyunsaturates from their triglycerides, regardless of the source of the triglycerides.

Mixtures of free fatty acids can also be separated from their natural sources by a transesterification process. The fatty acid containing material (marine animal oil, linseed oil, soybean oil, etc.) is refluxed with dry ethanol or dry methanol and a trace amount of sodium metal. This forms the ethyl or methyl esters, respectively, of the free fatty acids, liberating them from the triglyceride molecules. This method involves substantially milder conditions than basic hydrolysis, and prevents darkening of the reaction mixture from harsh conditions. The esters can be converted to free fatty acids at any stage of the extraction procedure by standard hydrolysis techniques. For some purpose it may be desirable to use the esters directly without conversion to the free acid form.

In the next step, the non-saponifiable materials, such as cholesterol, vitamins A and D and hydrocarbons, are removed by washing with an organic solvent. Any organic solvent, such as petroleum ether, methylene chloride, ethyl ether, etc., may be used for this purpose.

After removal of the organic phase, the aqueous phase is acidified. Any acid may be used for this acidification step, although pharmaceutically acceptable acids are preferred. This will cause the free fatty acids to separate into a separate organic phase. The aqueous phase is then discarded. The addition of a small amount of sodium chloride or other salt will enhance the separation.

The fatty acid mixture is next submitted to a urea treatment in order to remove saturated and mono-unsaturated fatty acids. In the urea treatment, urea is added to a polar organic solvent capable of readily dissolving both urea and the fatty acids therein. Examples of operable solvents include methanol, ethanol, isopropanol, petroleum ether, benzene, trichloroethylene, and methyl isobutyl ketone. Ethanol is preferred in order to avoid toxicity problems. The urea is dissolved in the solvent, if necessary with heating, to obtain a urea solution which normally contains from 10 to 20% of urea. The urea solution and the fatty acid mixture are mixed together. While the fatty acid mixture may be added to the urea solution, it is preferred that the fatty acid mixture first be diluted in additional organic solvent in order to provide some degree of protection for the fatty acids against the elevated temperature of the urea solution. The free fatty acids may be dissolved in petroleum ether or other polar solvents such as acetone, ethanol, or methanol. The amount of the urea solution is adjusted to be at least 0.5 parts by weight, preferably 1-4 parts, relative to each part by weight of the fatty acid mixture. The urea solution is mixed homogeneously with the fatty acid mixture.

The urea is then precipitated, preferably by cooling the urea-treated solution. At this time, saturated and mono-saturated fatty acids in the fatty acid mixture will form a complex with the urea crystals and precipitate out. The cooling may be conducted by leaving the solution to stand for a long period of time, if desired. The solution may also be forcibly cooled, for example by use of a water bath. Good results will be obtained when the solution is cooled to a temperature of at most 50° C., preferably from 30°-40° C. To obtain an even better urea removal, the solution may be further cooled in a refrigerator to about −10° C.

The complex of urea with saturated and mono-unsaturated fatty acids is then filtered off or otherwise removed. The filtrate solution obtained is concentrated, for example in an evaporator, to remove the major portion of the solvent, and then any remaining urea is washed from the fatty acid mixture with 5% hydrochloric acid. The solvent may also be removed by water extractions using 10 parts of water to one part of solvent.

The remaining fatty acid mixture is a substantially pure combination of higher unsaturated fatty acids. It has been discovered that these individual fatty acids may be completely separated in a very simple and accurate method by first dissolving them in an organic solvent, such as acetone, and then gradually cooling until the desired fatty acid solidifies out of the solution. As the solution is gradually cooled, various fatty acids, depending on their individual solubility in the solvent, precipitate. As each of these fatty acids precipitates, it is removed from the solution. The various fatty acids have specific points at which they precipitate from solution, depending upon their concentration in the solution. For example, it has been discovered that DHA precipitates from a 10% acetone solution at about −38° to −40° C. EPA precipitates at about −60° C. Most other fatty acids precipitate at temperatures above −30° C.

The solution is cooled in a bath of frozen carbon dioxide (dry ice) in acetone. The precipitate which forms at −38° to −40° C. is removed by filtration through sintered glass or a Buchner funnel without substantially raising the temperature. Analysis of the obtained crystals shows substantially pure DHA; NMR studies show no cis-trans conversion.

The substance precipitating at about −60° C. has been shown to be substantially 100% pure EPA with no cis-trans conversion.

In order to avoid the extremely low temperatures required to separate EPA and DHA separately, the volume of the supernatant can be reduced after each crystallization to reduce the solubility of the fatty acids, yielding a mixture of substantially pure DHA and EPA.

The solvent reduction method of low temperature fractional crystallization may be accomplished using the combination of higher unsaturated fatty acids which are obtained as a result of the urea treatment step discussed in detail above. The combination of higher unsaturated fatty acids obtained by the urea treatment step is solved in the same type of organic solvent as is used for the reducing temperature method; for example, is to be placed into a 10% solution of acetone or petroleum ether. When cooled overnight to about −20° C., any remaining saturated fatty acids and various fatty acids with low degree of unsaturation solidify out of the solution. The precipitate is then removed and discarded. The solution is then reduced in volume and increased in concentration by evaporation or distillation of the solvent to a predetermined fraction of its original volume, for example, one third of its original volume. When the reduced volume solution is again cooled to about −20° C., new crystals of mono-unsaturated fatty acids appear which crystals are again filtered out. The filtrate may then again be reduced by a factor of about one half to one nineth of its original volume and again cooled overnight to −20° C. Di-unsaturated fatty acids will now solidify out of solution. These crystals may again be filtered out and discarded.

To be sure that all undesired fatty acids have crystallized from the solution, the filtrate may be cooled further to −30° C. If no crystals appear, then the purification is complete. The solvent may then be evaporated.

The remaining liquid consists of a substantially pure combination of EPA and DHA. If desired, these two components may be separated by cooling to −38° to −40° C. to precipitate the DHA.

Patients suffering from diabetes mellitus were treated with sardine oil containing DHA in the triglyceride form, and with sardine oil after hydrolysis of the acids and removal of the glycerine. The study was conducted for 25 days. Each patient took three teaspoons per day, and did not change his dietary habits or medications in any way. The control group was administered three teaspoons of peanut oil each day.

The results of the test are tabulated below.

| | Adult Diabetics - blood Glucose (mg %) | | | | | |
|---|---|---|---|---|---|---|
| | Control peanut oil | | Fish oil (Triglyceride) | | Free Fatty Acid | |
| | Beginning of Study | After 25 days | Beginning of Study | After 25 days | Beginning of Study | After 25 days |
| 1 | 250 | 240 | 280 | 240 | 250 | 110 |
| 2 | 170 | 180 | 120 | 120 | 180 | 105 |
| 3 | 200 | 200 | 340 | 280 | 240 | 115 |
| 4 | 240 | 230 | 290 | 250 | 200 | 105 |
| 5 | 320 | 300 | 370 | 300 | 320 | 130 |
| 6 | 325 | 330 | 320 | 280 | 280 | 130 |
| 7 | 290 | 310 | 315 | 300 | 120 | 100 |
| 8 | 380 | 370 | 200 | 200 | 340 | 200 |
| 9 | 280 | 280 | 240 | 200 | 290 | 150 |
| 10 | 300 | 290 | 170 | 150 | 370 | 100 |
| 11 | 180 | 200 | 250 | 200 | 320 | 140 |
| Average | 266.8 | 266.4 | 263.2 | 229.1 | 264.6 | 125.9 |
| S.D. | ±62.7 | ±57.9 | ±72.7 | ±57.6 | ±71.9 | ±28.4 |

It will be obvious to those skilled in the art that various changes may be made without departing form the scope of the invention, and the invention is not to be considered limited to what is described in the specification.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A method for treating diabetes mellitus comprising administering to a patient suffering from diabetes mellitus an effective amount of a fatty acid selected from the group consisting of EPA, DHA, and a mixture thereof, said fatty acid being in the free acid form or in the form of a pharmaceutically acceptable salt thereof, said composition being substantially free of other fatty acids.

2. The method of claim 1 wherein the fatty acid is EPA.

3. The method of claim 1 wherein the fatty acid is DHA.

4. The method of claim 1 wherein the fatty acid is administered orally.

5. The method of claim 1 wherein the fatty acid is administered parenterally.

6. A method in accordance with claim 1 wherein said fatty acid is the mixture of free fatty acids obtained by hydrolysis of the triglycerides obtained from fish oil to obtain free fatty acids and glycerines, and removal of the glycerine.

7. The method of claim 6 wherein said mixture is administered orally.

8. The method of claim 6 wherein said mixture is administered parenterally.

9. A method in accordance with claim 1, wherein the fatty acid is a mixture of EPA and DHA.

10. A method for treating diabetes mellitus comprising administering to a patient suffering from diabetes mellitus an effective amount of a composition consisting essentially of a fatty acid selected from the group consisting of EPA, DHA, and a mixture thereof, said fatty acid being in the free acid form or in the form of a pharmaceutically acceptable salt thereof.

* * * * *